United States Patent [19]
Balkanli

[11] Patent Number: 5,389,216
[45] Date of Patent: Feb. 14, 1995

[54] METHOD FOR ACTIVE CORROSION ANALYSIS

[76] Inventor: Hayati Balkanli, P.O. Box 35725, Houston, Tex. 77235

[21] Appl. No.: 46,200

[22] Filed: Apr. 14, 1993

[51] Int. Cl.⁶ ............................................. G01N 17/00
[52] U.S. Cl. ............................................. 204/153.11
[58] Field of Search ............... 204/147, 153.11, 196, 204/404

[56] References Cited

U.S. PATENT DOCUMENTS

| | | | |
|---|---|---|---|
| 2,943,027 | 6/1960 | Schaschl | 204/153.11 |
| 4,658,365 | 4/1987 | Syrett | 364/496 |
| 5,241,301 | 8/1993 | Rivola | 340/660 |

OTHER PUBLICATIONS

European Patent Application 0 411 689 A1 Rivola, Luigi Feb. 6, 1991.

*Primary Examiner*—John Niebling
*Assistant Examiner*—Brendan Mee
*Attorney, Agent, or Firm*—Gunn & Kuffnep

[57] ABSTRACT

A method, for measuring the parameters of cathodic protection of the structures which are protected by electrolysis or by sacrificial anodes, comprises fixed programs for executing data acquisition and processing, measurement steps with high speed data sampling and digitizing in the passive and active modes of operation, generating a constant current pulse being sourced into or sunk from electrolyte containing said structures while in a measurement step, and generating a forced off-state condition in the vicinity of a test point of said structures. And, an active corrosion analyzer, (for implementing said method for measuring the polarized potential, the IR-drop, the depletion region capacitance, the coating capacitance, the equivalent voltage, and the equivalent resistance), comprises a microcontroller, a precision timing generator, a non-volatile memory, a random access memory, an analog to digital converter, constant current generators, and control elements.

16 Claims, 5 Drawing Sheets

METHOD FOR ACTIVE CORROSION ANALYSIS

FIELD OF INVENTION

This invention relates to cathodic protection of buried structures against corrosion by electrolysis and, specifically to the direct measurement of the IR drop and polarized potential (ion concentration), without interrupting the current supporting electrolysis. This invention also deals with other parameters of the system that are either ignored or could not be directly measured by the prior art devices. Some of these parameters are the IR drop, the equivalent resistance, the depletion region capacitance, the coating capacitance, and the ion recombination time in the vicinity of a test point of the structure cathodically protected.

A patent search revealed several U.S. Patents teaching the use of special generators for interrupting the impressed current supporting electrolysis to make a measurement of polarizing potential only. The U.S. Pat. Nos. 3,634,222; 3,841,988; 4,080,272; 4,383,900; and 4,823,072.

DESCRIPTION OF A CATHODICALLY PROTECTED SYSTEM

FIG. 1 shows the context exemplified by a buried pipeline which is protected against corrosion by electrolysis, and which is designated as the protected system 10. The electrolysis is supported by a current flow from a buried metal anode 2 toward the pipe 1 through the ground surrounding the pipe. The current supporting electrolysis is supplied by a generator 3 which is commonly a full wave rectifier. This current is also referred as the impressed current. The voltage applied between the anode and the pipe causes hydroxyl ions to move toward the anode while the hydrogen ions move toward the pipe. In the vicinity of the pipe, however, the positively charged hydrogen ions are discharged by picking up conduction electrons. This causes the formation of a region void of surplus charges namely, the region around the pipe and causes formation of a depletion region capacitance. The ground resistance between the pipe and the anode is represented as two equivalent resistors R1 and R2 at the point 33 where the probe 9 is inserted into the ground with its tip 91. The resistive material is not lumped; rather, it is distributed in the surrounding medium such as the earth and is depicted as shown in the drawing. The two resistors R1 and R2 form an equivalent resistor defined by fundamental circuit relationships once the lumped values are defined. The probe is a half cell having a non-conductive, transparent, cylindrical enclosure filled with saturated copper sulfate as an electrolyte. A copper rod, one end being in a feed through configuration and collinearly enclosed with the enclosure as electrode, is used to close one end of the probe enclosure. Also, a porous ceramic tip, making electrical contact with the ground by wetting the contact area, is used to plug the other end of the probe. The current supporting electrolysis is designated as Ig. The voltage at the point of 33, which is referred to as the ON state voltage in the prior art, will be labelled as the equivalent voltage (Ee) hereinafter. It is commonly established that the equivalent voltage is the sum of the two voltages which are referred to as the IR drop and the polarized potential, and they are used in equation (1):

$$Ee = (Ig)(R2) + Ep \quad (1)$$

where Ep is the polarization potential which is a potential dependent on the concentration of the hydroxyl ions between the pipe and the anode.

The concept of protecting a corrodible material by electrolysis is applicable to a wide variety of structures surrounded by an electrolyte or a semi-electrolyte medium to support electrolysis such as underground and underwater steel structures. In most applications of this invention, only a semi-electrolyte (a moist soil) supports electrolysis around the underground structures while this invention is readily applicable to offshore platforms and pipelines in contact with an electrolyte such as sea water also supporting electrolysis. By measuring the ground potential generated by the current flow from an anode to a pipe as shown in FIG. 1, the extent of corrosion protection of the pipe can be evaluated with this invention without interrupting the protective current.

PRIOR ART

The patents noted above clearly indicate that the prior art concentrated on the measurement of the OFF state voltage at a test point by interrupting the impressed current for relating to the hydroxyl ion concentration. This is due to the fact that the hydroxyl ions have very low mobility while the impressed current is flowing, and after the impressed current is interrupted. Their mobility decreases due to the absence of the electric field provided by the generator. Therefore it becomes very easy to measure the polarized potential with a handheld voltmeter. Whenever the impressed current is interrupted, the electric field intensity generated by the hydroxyl ions starts decaying exponentially due to the recombination of the ions in the absence of the current.

The causes of the inaccuracy of this type of measurement is explained in the U.S. Pat. No. 3,634,222 by the inventor. To improve the accuracy of the measurement, the inventor introduced the periodical switching interruption of the anode current. That is, the anode current is periodically turned off. Then, following with a delay of 0.2 second, the cathode reference potential is cyclically and periodically sampled during the off period of the anode current. The sampled cathode reference potential is compared with the established reference value of 0.85 volt and the anode current is automatically adjusted to elevate the cathode reference potential to the established reference level.

U.S. Pat. No. 3,841,988 also teaches a similar approach for the same measurement with the addition of another probe and a differently implemented switching circuit. This patent, however, mentions that the current requirement changes as a function of the surface geometry of the cathodically protected structure. Also, it introduces the "overprotection" phenomenon, which causes damage to the paint of coated structures. At certain locations of the structure the anode current may exceed a desired level and cause disbonding of the coating by generating excessive hydrogen ions.

U.S. Pat. No. 4,080,272 introduces the synchronization of the sampled reference voltage with that of the minimum voltage region of the fullwave rectified waveform of the generator supplying the anode current. The second and the third references also use similar switching circuits. This reference, however, reduces the effect of the switching transients. U.S. Pat. No. 4,383,900 argues that the previous art is not effective because they do not sample and track the minimum potential. This reference also claims that the continuous interruption of the impressed current keeps the protected system in the continuous dynamic state, and the impressed current does not fall to zero as presumed. To overcome this while reducing the impressed current to zero, it teaches one to shortcircuit the output terminals of the power supply by a transistor switch. Stating that this invention measures the true polarized potential. This invention, however, ignores the discharge time of the system capacitances during the shortcircuit period.

U.S. Pat. No. 4,823,072 teaches the use of an elaborate switching circuit with each generator supplying the impressed current. In reference to a pipeline, having several generators, this patent states at column 2, from line 27 to 29, "Thus, for the interruption system to work, the interruption must be synchronized so that all interruptions occur simultaneously". To overcome such an undertaking, it introduces another switching circuit which interrupts the impressed current for 0.25 second at every 4.25 seconds. It also notes the shortcomings of the previous art.

In summary, the prior art teaches the use of the switching circuits which periodically turn off the generator, thereby interrupting the electrolysis while measuring the polarized potential. The conditions at a test point would be as measured if there were only one generator supplying the impressed current for electrolysis. In fact, many generators are used for improving the effectiveness of the electrolysis. The conditions at a test point are generated by the cumulative effects of many impressed currents supplied by the generators. This fact forced the prior art devices to increase the turn off time to obtain a time window for the measurement which, in return, reduced the effectiveness of the electrolysis. In addition to the above mentioned switching problems of the prior art, the depletion region capacitance, whose existence is disclosed by this invention, is a prime factor causing an increased turn off time. The discharge time of the depletion region capacitance is a function of the ground resistance and condition of the semi-electrolyte. These prior art methods are either inaccurate or expensive to implement. Many of these are made for a single structure limited to a single generator. Furthermore, each method still requires a passive analyzer to make a measurement in protected systems such as buried pipelines. The limitations of the prior art can be traced to the inaccuracy of the modeling of the cathodically protected systems by the prior art. Namely, the above mentioned references accepted and treated the protected systems as discrete components. In reality, the protected systems are multidimensionally distributed values, not point values, from the perspective of the ,electric field in which the pipelines are placed, even though they may be a single structure such as the hull of a ship, an offshore platform, or a steel reinforced concrete building. A buried pipeline is an excellent example of a system best treated as a distributed system in the cylindrical coordinates. If a cylindrical electric field provides the cathodic protection, the magnitude of the impressed current can be minimized to provide optimal economic protection. In short, if an isoelectric field is generated around a structure placed in an electrolyte or semi-electrolyte, the cathodic protection is totally effective. Also, if cathodic protection is measured without interrupting the impressed current as disclosed in this invention, there are no switching transients to eliminate or delay the measurements. Hence, the cost of the cathodic protection system is optimized.

In short, this invention eliminates costly power supplies and avoids switching transients by measuring the parameters of cathodic protection without interrupting the impressed current.

BACKGROUND AND SUMMARY OF THE INVENTION

The background of this invention started with replacing a handheld voltohmmeter for measuring the resistance of the electrolyte. Tests conducted both in the field and in the laboratory using a handheld voltohmmeter indicate different values for the ground resistances for the coated and bare pipes in the same locale. Also, due to logarithmic ohm scales, meter inaccuracy is intolerable at the higher resistivity scales. A simple solution, such as injecting a constant current into the ground and measuring the voltage drop caused by the constant current, may replace the handheld meter. Especially, if the current is one milliampere or one microampere, it is very simple to convert the voltage drop into kilohms or megohms, respectively. A bilateral constant current generator circuit was implemented and extensive tests were conducted in the laboratory along with testing in the field. The bilateral constant current generator was input to an HP 3312A function generator, and the resultant voltage waveforms were investigated. The tests established that a forced off state condition can be generated by adjusting the magnitude of the current injected into the electrolyte at a test point without interrupting the electrolysis process. Further tests were conducted to investigate the rise and fall times of the waveforms for calculating the capacitance. These tests proved the existence of the above mentioned capacitances which caused the disappearance of the waveform generated by the fullwave rectifiers used in the prior art.

In summary, this invention provides a method and an apparatus for measuring the pertinent parameters of a buried pipeline or of an offshore platform to be protected against corrosion by electrolysis without interrupting the impressed current of electrolysis or restricting the generator to any specific waveform. Several parameters and the methods of their measurements in the vicinity of a test point of a cathodically protected structure based on this invention are;

1. The equivalent voltage $E_e$, elsewhere named ON state Voltage, is measured at a fixed rate of sampling and digitization, 2. The equivalent resistance $R_e$ is by measured from the resultant voltage drop caused by an active signal and calculation, 3. The depletion region capacitance $C_d$ is measured from the rise time $\tau$ of the resultant voltage drop caused by a constant current pulse directed into the electrolyte, and calculation from the relationship:

$$\tau = (C_d)(R_e),$$

4. The coating capacitance $C_c$ is measured from the rise time of the voltage drop caused by a constant current pulse into the electrolyte across the equivalent resistance $R_e$ and calculation from the relationship:

$$t = (C_c)(R_e),$$

5. The IR drop is measured from the voltage drop caused by the impressed current supporting electrolysis while measuring the rise time of the voltage drop immediately following a forced off condition which is then terminated, 6. The polarized potential Ep is defined by the equivalent voltage (Ee) and IR drop by calculation as represented in equation (1) above, and 7. Ion recombination time, following the IR drop measurement is from measurements of the equivalent voltage change as a function of time and calculation.

BRIEF SUMMARY OF OPERATION OF THE ANALYZER

Going to FIG. 2, when power is applied to the processing module 200, it automatically resets the analyzer. Then, upon a manually initiated SET pulse, the processing module 200 initiates and completes a data acquisition cycle through internally generated clock pulses and measures the above mentioned parameters. The measured data is stored in a memory for operator review or transfer to a computer through a serial port for further processing. During the first clock pulse period, the equivalent voltage Ee is measured. At the leading edge of the second clock pulse, the processing module 200 initiates a constant current pulse into ground through the data acquisition module 100 while measuring the resultant voltage drop and the rise time of the pulse. Since the magnitude of the constant current pulse is fixed and known, the processing module 200 calculates the values of the equivalent resistance and depletion region capacitance from the voltage drop and its rise time measurements. During the third clock pulse period, the processing module 200 will sink a constant current pulse from ground via data acquisition module 100 while measuring the voltage drop and its rise time for calculating the coating capacitance. During the fourth clock pulse period, the processing module 200 will generate a forced Off state condition in the vicinity of a test point by generating a stepwise increasing constant current pulse to be sunk from ground through the data acquisition module 100 and the Probe 9 while comparing the resultant equivalent voltage with zero level. As soon as an Off-state condition is achieved, the processing module 200 will terminate it and allow the ground current (Ig) to take effect and measure the voltage drop across the equivalent resistance and its rise time during the fifth clock pulse period. The processing module 200 will extract the IR drop and polarized potential from the data stored during the first and fifth clock pulse periods. The detailed operation of the analyzer will be covered in the description of the preferred embodiment.

BRIEF DESCRIPTION OF THE DRAWINGS

For clarity, an embodiment of the invention is described hereinafter as illustrative with but not restrictive, reference to the annexed drawings in which.

DESCRIPTION OF THE PREFERRED EMBODIMENT

Figure 1:
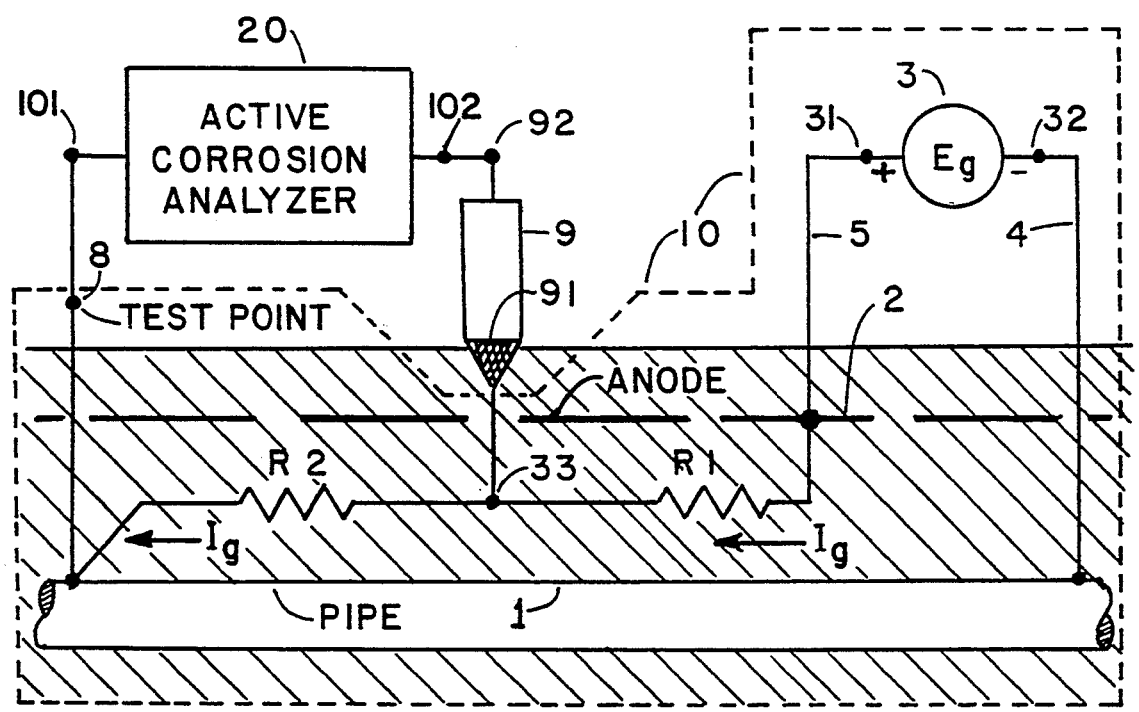
FIG. 1 depicts a simplified descriptive diagram of a corrosion protected system 10 comprising a generator 3, an anode 2, and a pipe 1, including an active corrosion analyzer 20 and a probe 9 for making a measurement between a test point 8 and ground through the tip 91 of the Probe 9.
Figure 2:
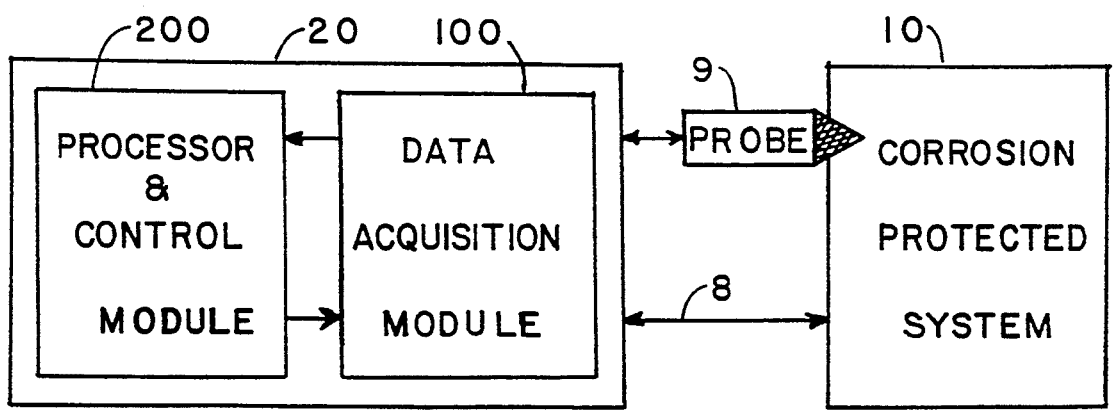
FIG. 2 is a simplified block diagram of the corrosion protected system 10 and an active corrosion analyzer 20 operating both in the passive and active modes in the vicinity of a test point of the protected system.

In the description, which follows, like parts are designated throughout the specifications and drawings with the same numerals respectively. Referring now to FIG. 1, the relationship between an active corrosion analyzer 20 and a corrosion protected system 10 is depicted in the both active and passive modes of operation. A generator 3, preferably a full wave rectifier, but not restricted to any construction is connected to the pipe 1 through its negative terminal 32 with an insulated wire 4, and to the anode 2 through its positive terminal 31 with an insulated wire 5. When the generator is turned on and adjusted to the proper voltage level, a current Ig starts flowing from the anode 2 toward the pipe 1 in the soil and thereby initiates the process of electrolysis. For measuring the parameters involved with electrolysis, an active corrosion analyzer 20 is connected to a test point 8 through its terminal 101, and to ground through its terminal 102 via the input terminal 92 of the probe 9. The probe 9 is stuck into ground at its tip 91 to make contact with the point 33 of the ground resistance, thereby dividing the ground resistance into two values or R1 and R2. Since the probe 9 is half of a galvanic cell, it enables the analyzer 20 to measure the potential gradient in the vicinity of a test point 8 without any degradation. As far as the analyzer 20 is concerned, the protected system 10 is just an open circuited branch containing a voltage source Ee and an equivalent resistance Re between the point 33 and the pipe 1 as shown in the FIGS. 3 through 7A.

Figure 3:
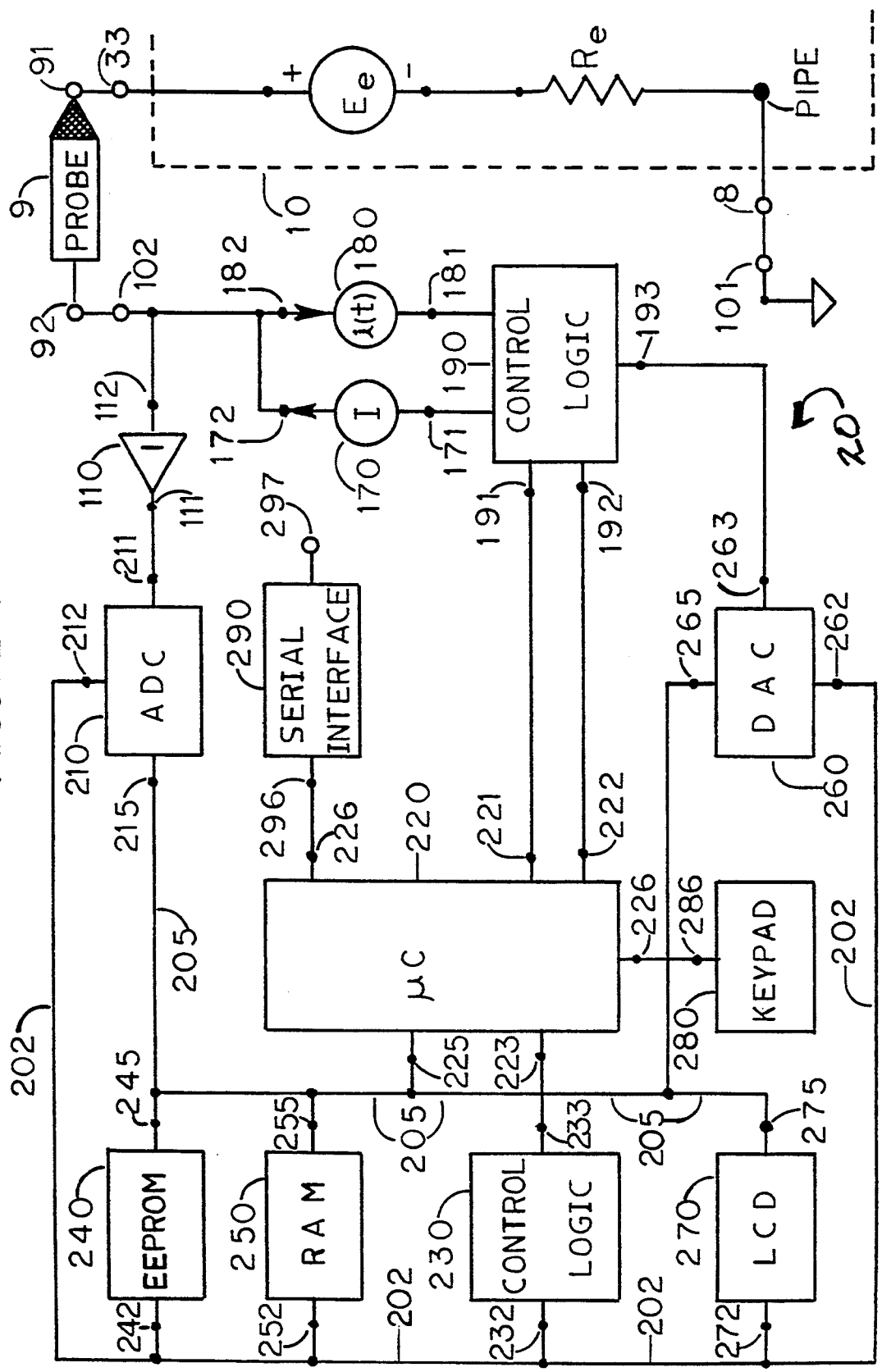
FIG. 3 is a functional block diagram of the processor control module 200 and the data acquisition module 100 which comprise the active corrosion analyzer, probe 9, and the steady state equivalent circuit of the corrosion protected system 10 in the vicinity of a test point 8 of the protected system 10.
Figure 8:
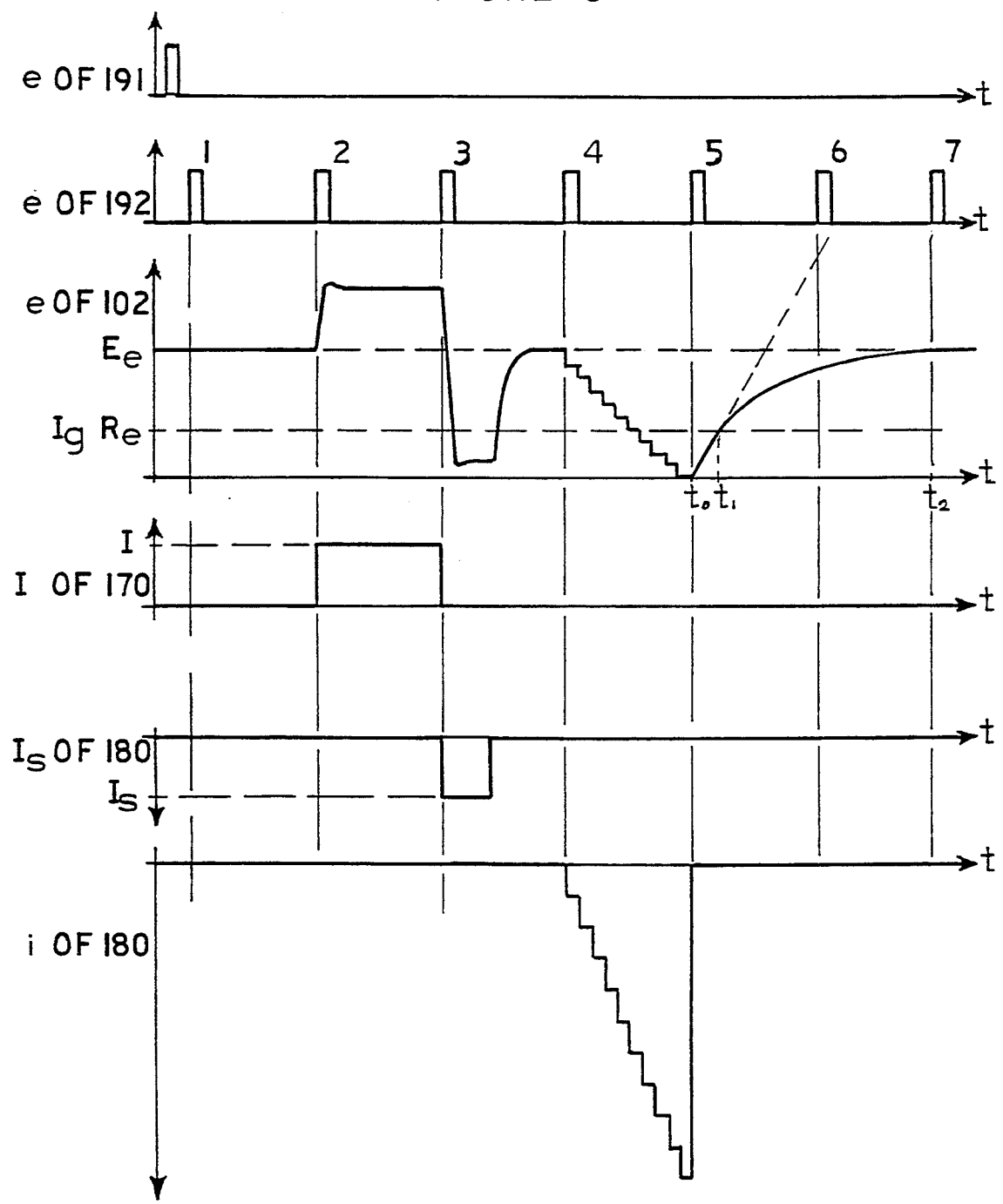
FIG. 8 depicts the timing diagrams of the active corrosion analyzer 20 in an individual data acquisition cycle.

With reference now to FIGS. 3 and 8, a detailed description of the active corrosion analyzer 20 including descriptions of the submodules, and its operation, with the protected system 10 will follow. In FIG. 3, a corrosion protected system 10 is represented by its Thevenin's equivalent circuit in a steady state condition, after all electrical transients are ended. The generator 3 and the anode structure 2 are not shown in FIG. 3. However, the reflected component of the generator Eg, the reflected component of ion concentration Ei, and the voltage drop (Ig R2) caused by the ground current Ig across the resistance R2 are shown as a single voltage source, the equivalent voltage Ee, with the polarity as indicated. The equivalent resistance Re is between pipe 1 and probe 9. Also, a test point 8 is connected to the pipe 1 with an insulated wire. The equivalent voltage Ee is placed in series with the equivalent resistance Re, between the tip 91 of the probe 9, in the ground and the pipe. The analyzer 20 is connected to the protected system 10 through the terminal 92 of the probe 9, the tip 91 and through the terminal 101 connected to the test point 8.

As mentioned before, the active corrosion analyzer 20 is composed of a data acquisition module and a processing and control module 200. The data acquisition module 100 is composed of an amplifier 110, a constant current source 170, a time variable current sink 180, and control logic 190. The amplifier 110 monitors the voltage at the terminal 102 with its input terminal 112, and transfers the voltage to the input terminal 211 of the analog to digital converter 210 via its output terminal 111 during the active and passive modes of operation. The control logic 190 is connected to the terminals 221 and 222 of the microcontroller 220 through its input terminals 191 and 192, and to the output terminal 263 of the digital to analog converter 260 through its input terminal 193. The control logic 190 activates the current source 170 or the current sink 180 during the active mode of operation of the analyzer 20. In the passive mode of operation of the analyzer 20, however, the current source 170 and the current sink 180 are inactive. Their output terminals 172 and 182 represent an open circuit for the data acquisition terminal 102. It is important to note that the ports of the submodules may have several terminals and they may be assigned to different functions. If the terminals of a port are assigned to different functions, they will be referred as terminals in this disclosure.

The processor and controller module 200 includes a microcontroller 220, and analog to digital converter (ADC) 210, an EEPROM 240, a RAM 250, a control logic 230, a liquid crystal display (LCD) 270, a keypad 280, and a digital to analog converter (DAC) 260. The control port 212 of the ADC 210, the control port 242 of the EEPROM 240, the control port 252 of the RAM 250, the control port of the LCD 270, the control port 262 of the DAC 260, and the output port 232 of the control logic 230 are all connected to the control bus 202. The control signal to the control logic 230 is supplied to its input port 233 from the control port 223 of the microcontroller 220. The output port 215 of the ADC 210, the data I/O port 245 of the EEPROM 240, the data I/O port 255 of RAM 250, the data input port 275 of the LCD 270, the data input port 265 of the DAC 260, and the data I/O port 225 of the microcontroller 220 are all connected to the data bus 205. The analyzer 20 is operator controlled through the keypad 280 which is connected to the control port 226 of the microcontroller 220. Also, a serial interface module 290 is connected to the serial data interface port 226 of the microcontroller 220 for transmitting the information collected to a computer through the data output port 297.

Now the specifications of the submodules shown in FIG. 3 and some components used in the submodules shown in the FIG. 3 and some of the components used in the submodules will be presented for implementing the design of the active corrosion analyzer 20 disclosed above. As mentioned above, the basic concept is to measure the nodal voltage changes of the terminal 102 while injecting a preset signal to the ground through the terminal 102. This implies that two functions are performed simultaneously. In order to accomplish this, the control logic submodules 190 and 230 control operation. Since the analyzer 20 is targeted for field use, reduced power consumption is an important design parameter (requiring minimum power consumption) in selecting components. With this consideration in mind, an eight bit CMOS microcontroller 80C51 is preferred. This device has four I/O ports which are eight bits wide, two 16 bit counter/timers, one $128 \times 8$ RAM, one full duplex serial channel, and a Boolean processor. It consumes 25 mA current in the active mode, only 4.4 mA in the idle mode, and 0.050 mA in the power down mode. It is capable of executing an instruction in 48 clock pulse periods at the longest. At an oscillator frequency of 16 MHz, this corresponds to 3 microseconds. The EEPROM 240 was selected with a configuration of $8K \times 8$ CMOS memory for two purposes. The first purpose is to store the functional programs required for data acquisition, storage review, and calculations. The second purpose is to provide additional memory space for storing the data collected. This submodule is also selected to provide flexibility for modifying the functional programs. The submodule RAM 250 is a nonvolatile random access memory with a configuration of $32K \times 8$ for data storage. The non-volatile state is maintained by a backup battery. Accuracy depends on the ADC 210, the DAC 260, and the amplifier 110. Consequently, the ADC 210 and DAC 260 are 12 bit high speed converters. There are several ADC & DAC submodules available in the market meeting the above mentioned specifications. As for the amplifier 110, again there are abundant precision, operational or instrumentation amplifiers in the market to make a selection for maintaining the 12 bit accuracy of the specification mentioned above. The current generators 170 and 180 have identical circuits and are implemented with identical, precision operational amplifiers similar to model LT1007. A bilateral constant current generator circuit is referenced to "General Purpose Linear Devices Data Book, 1989, National Semiconductor Co.", page 3–368. As commonly practiced by electronic engineers, the amplifier 110 is shown to have unity gain in the FIG. 3. The control logic submodule 230 control operation with components referenced in "RCA COS/MOS Integrated Circuits " Copyright 1977 and "RCA High-Speed CMOS Logic ICs," Copyright 1986, and connects to various submodules by the control bus 202. Also, the control logic 190 utilizes similar devices to select and activate the current generators 170 and 180 in timed operation. The logic devices used in the implementation of the Analyzer 20 are standard 4000 and 7400 series CMOS devices. The keypad 280 is a commonly available, 3×4 matrix, membrane switch. The LCD 270 submodules is a two-line, 16 character, microcontroller compatible, liquid crystal display manufactured by several companies.

With reference now to FIGS. 3 and 8, a detailed description of the operation of the active corrosion analyzer 20 is as follows: As soon as the power to the analyzer is turned on, the microcontroller 220, having a precision clock pulse generator resets the active corrosion analyzer 20. After the power is applied, operator control via a manual set switch located on the keypad 280 is momentarily actuated and the microcontroller 220 transmits a set pulse to the control logic 190 from the terminal 221 to the terminal 191. Timing of the set pulse is shown in FIG. 8, at the top curve identified at 191. Following the set pulse, the microcontroller 220 periodically generates seven clock pulses transmitted to the terminal 192 of the control logic 190. The seven pulses are shown in the second curve of FIG. 8 and bears the reference numeral 192.

During the first clock pulse period, the amplifier 110 monitors the ground potential through the terminal 102 and transfers the analog voltage to the ADC 210 through the terminal 211 to be digitized with a rate of one data word every 10 microseconds. The data, sampled during the first clock pulse period and exemplified as Ee in FIG. 8, is averaged and stored in the RAM 250. To average five samples, it takes approximately 60 microseconds to store one data word in the RAM 250. This establishes a 60 microsecond cycle as shown in the first clock pulse period.

In FIG. 8, at the rising edge of the second clock pulse, the control logic circuit 190 activates the constant current generator 170. A constant current pulse is shown in FIG. 8, identified as I of 170, and flows into ground through the tip 91 of the probe 9. During the second clock pulse period, while the constant current pulse I flows from the current generator 170 into ground, the voltage at the terminal 102 is monitored by the amplifier 110, digitized by the ADC 210, and stored in the RAM 250 when the control logic 190 frees the microcontroller 220 for data sampling during the second clock pulse period. The effect of this current on the voltage drop being monitored during the second clock pulse period is shown as a voltage pulse and is illustrated in FIG. 8 as the voltage "e of 102". The measurement of the rise time of the voltage pulse is accomplished at a high rate of sampling and digitizing prior to the steady state condition of the current pulse I of the current source 170. Then, the calculation of the depletion region capacitance is undertaken. The second clock pulse duration can be estimated similarly to that of the first clock pulse period. If it is assumed again that five samples are taken following the rise and ringing of the voltage pulse and 100 microseconds are allowed for the rise and ringing time, then the second clock pulse period may not be less than 160 microseconds. If the calculations of the equivalent resistance Re and depletion region capacitance are completed during the second clock pulse period, the second clock pulse period is around 180 microseconds. In the drawings of FIG. 8, the rise and fall times of the voltage pulses are slightly exaggerated for emphasizing the existence of the charging times of the depletion region and coating capacitances via the equivalent resistance during the second, third and fifth clock pulse periods of FIG. 8.

At the rising edge of the third clock pulse, the control logic 190 activates the constant current generator 180 and a current pulse is sunk from ground through the tip 91 of the probe 9 through the terminal 102. This pulse is shown in FIG. 8 at the timed event on the curve 180. During the duration and rise time of the current pulse Is at 180, the voltage of the terminal 102 is monitored by the amplifier 110 and digitized by the ADC 210 with a rate of 10 microseconds while the current pulse flows. The magnitude of the current pulse Is is purposely selected to be large enough to cause a negative voltage drop at the terminal 102. If the voltage at the terminal 102 is negative, the depletion region capacitance Cd is eliminated. This will leave only the coating capacitance Cc to account for the rise time of the voltage waveform if the pipe is painted. It is important to note that, if the pipe is painted, the rise time measured in the second clock pulse period will be shorter than that of the rise time measured in the third clock pulse period because the two capacitances are in series. During the rest of the third clock pulse period, the equivalent resistance Re and coating capacitance Cc are calculated by the microcontroller 220 and the results are stored in the RAM 250. It can be concluded that if the rise time associated with the measurement of the third clock pulse period is much smaller than that of the rise time measured in the second clock pulse period, the pipe has no coating. This is due to the fact that the current pulse Is eliminates the depletion region and its capacitance. If the rise time of the voltage Ee at 102 measured in the third clock pulse period is larger than that of the rise time measured in the second clock pulse period, then the pipe has a coating material on it.

During the fourth clock pulse period, however, the microcontroller 220 generates a stepwise increasing voltage waveform at the output terminal 263 of the DAC 260 while monitoring and digitizing the voltage at the terminal 102 until it becomes zero. The stepwise increasing voltage generated at the output of the DAC 260 will be transmitted to the terminal 193 of the control logic 190 starting with the rising edge of the fourth clock pulse. The stepwise increasing current pulse flows from ground in the vicinity of the test point but in the opposite direction to that of the ground current Ig. The stepwise increasing current generated during the fourth clock pulse period is shown in FIG. 8 and identified at i of 180. The effect of the stepwise increasing current at the terminal 102 is a stepwise deceasing voltage which is shown in FIG. 8 and indentified as e of 102. That is, the constant current generator 180 generates one current step in response to each voltage step produced by the DAC 260. Each current step flows through the equivalent resistance Re, the probe 9 and the terminal 102 while the microcontroller 220 is monitoring the voltage at the terminal 102 via the amplifier 110 and the ADC 210. This stepwise increasing current (see FIG. 8 at i of 180) will decrement the equivalent voltage Ee by the voltage drop it generates across the equivalent resistance Re at each step. As soon as the voltage e of 102 becomes zero, the microcontroller 220 terminates the stepwise increase of voltage at the output terminal 263 of the DAC 260 by injecting a digital zero to the input terminal 265 of the DAC 260. This reestablishes the flow of the ground current Ig in the vicinity of the test point and also initiate the fifth clock pulse period. The duration of the fourth clock pulse period depends on the magnitude of the equivalent voltage Ee. The time length of each decrementing step may be as short as 10 microseconds and depends primarily on the conversion rate of the ADC 210.

At the rising edge of the fifth clock pulse, the microcontroller 220 will resume digitizing the voltage at the terminal 102 by the ADC 210 and sequentially store the digitized data into the RAM 250 to extract the rise or fall time of the voltage waveform at the terminal 102. During the sixth clock pulse periods, the voltage at the terminal 102 is allowed to rise to its normal level Ee whch was measured during the first clock pulse period.

At the start or rising edge of the seventh clock pulse period, the microcontroller 220 terminates the data acquisition cycle according to the program stored in the EEPROM 240 while the control logic 190 resets itself and remains reset until the next SET pulse is manually generated by the system.

Figure 4A:
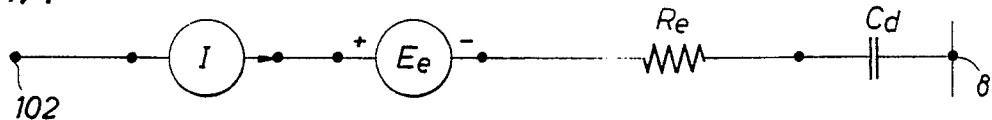
FIG. 4A represents the dynamic equivalent circuit of a corrosion protected system while a current pule I is input into ground.
Figure 4B:
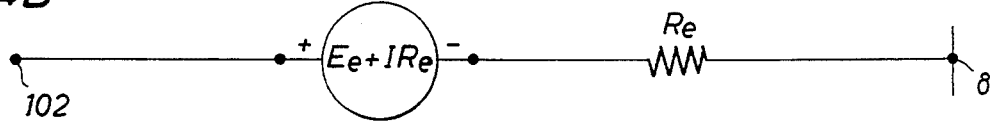
FIG. 4B represents a simplified equivalent circuit of a corrosion protected system 10 while the constant current pulse I is flowing.

In reference to FIGS. 4A and 4B, the dynamic equivalent circuit of the protected system 10, which is effective only during the rising and falling edges of the constant current pulse (See I of 170 in FIG. 8) is introduced. As previously mentioned, due to the electrolysis, the hydrogen ions move toward the pipe 1 and pick up conduction electrons to become molecules by recombination and are discharged, which in return generates a depletion region and forms the depletion region capacitance Cd as shown in FIG. 4A. Since this capacitance is not effective during the steady or static state condition of the system 10, it has been ignored by the prior art. This invention, however, first proves its existence and shows its importance as a parameter to be measured and evaluated in regards to corrosion. The value of this capacitance is measured by its charging time through the equivalent resistance Re by the current pulse or by the ground current Ig as referenced to FIGS. 4B and 6D respectively. As mentioned previously, FIG. 6C represents the forced Off state condition of the system 10 at the end of the fourth clock pulse period. The preferred embodiment utilizes the ground current Ig for determining the timing coefficient of the depletion region capacitance Cd as in the FIGS. 7B and 8 in relation to the waveform Ee of 102 in FIG. 8.

In reference to the FIGS. 4C and 8, the steady state equivalent circuit of the system 10 is introduced while the current I of 170 is flowing. The voltage drop caused across the equivalent resistance Re by the current I of 170 is represented as a voltage source (I Re) with the polarity as indicated. The effect of this voltage drop is shown in FIG. 8 as voltage rise above the level of Ee during the second clock pulse period. The voltages Ee and (I Re) can be shown as a single voltage source where two are added.

Figure 5A:
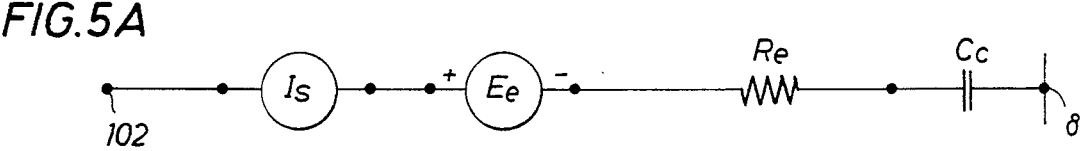
FIG. 5A represents the dynamic equivalent circuit of a corrosion protected system 10 while a current is input from ground.
Figure 5B:
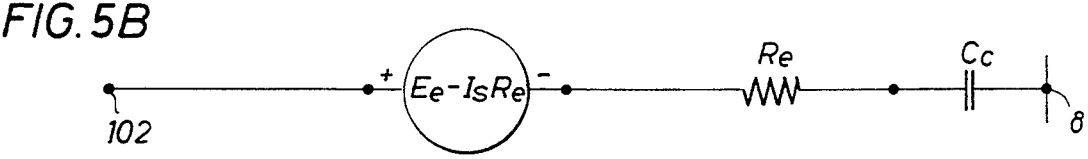
FIG. 5B represents a simplified equivalent circuit of a corrosion protected system 10 while a current Is is being input from ground.

In reference to FIGS. 5 and 8, the dynamic equivalent circuit of the protected system 10, which is effective only during the rising edge of the voltage E of 102 and during the current Is of 180 (in the third clock pulse period), is introduced. Because this current flows in a reverse direction to that of the ground current Ig, it eliminates the depletion region and its capacitance until the ground current becomes effective again.

Figure 6A:
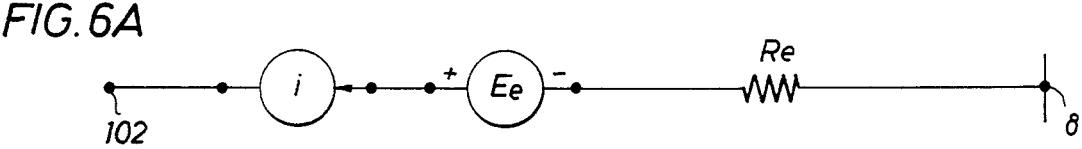
FIG. 6A represents the equivalent circuit of a corrosion protected system 10 in a steady state condition with a stepwise increasing current from ground.
Figure 6B:
FIG. 6B represents a simplified equivalent circuit of a corrosion protected system 10 while a step current is flowing.
Figure 6C:
FIG. 6C is the equivalent circuit of a corrosion protected system 10 while it is in an off condition.
Figure 6D:
FIG. 6D is the dynamic equivalent circuit of a corrosion protected system 10 when the Ground Current Ig is about to take effect at the end of the forced OFF state condition.

With reference also to FIGS. 6A and 6B, the steady state equivalent circuit is presented while each step current of the stepwise increasing current is flowing. The only difference from that current of FIG. 5 is that I of 180 decrements the equivalent voltage Ee stepwise until Ee becomes zero. In other words, the charge of the depletion region capacitance is decremented until it becomes zero. The outcome of this process is presented in FIG. 6C. The depletion region capacitance, however, is kept intact for the ground current Ig to charge up to the level of Ee in the fifth clock pulse period. That is, the effective current in the equivalent circuit is zero during the last current step.

Figure 7A:
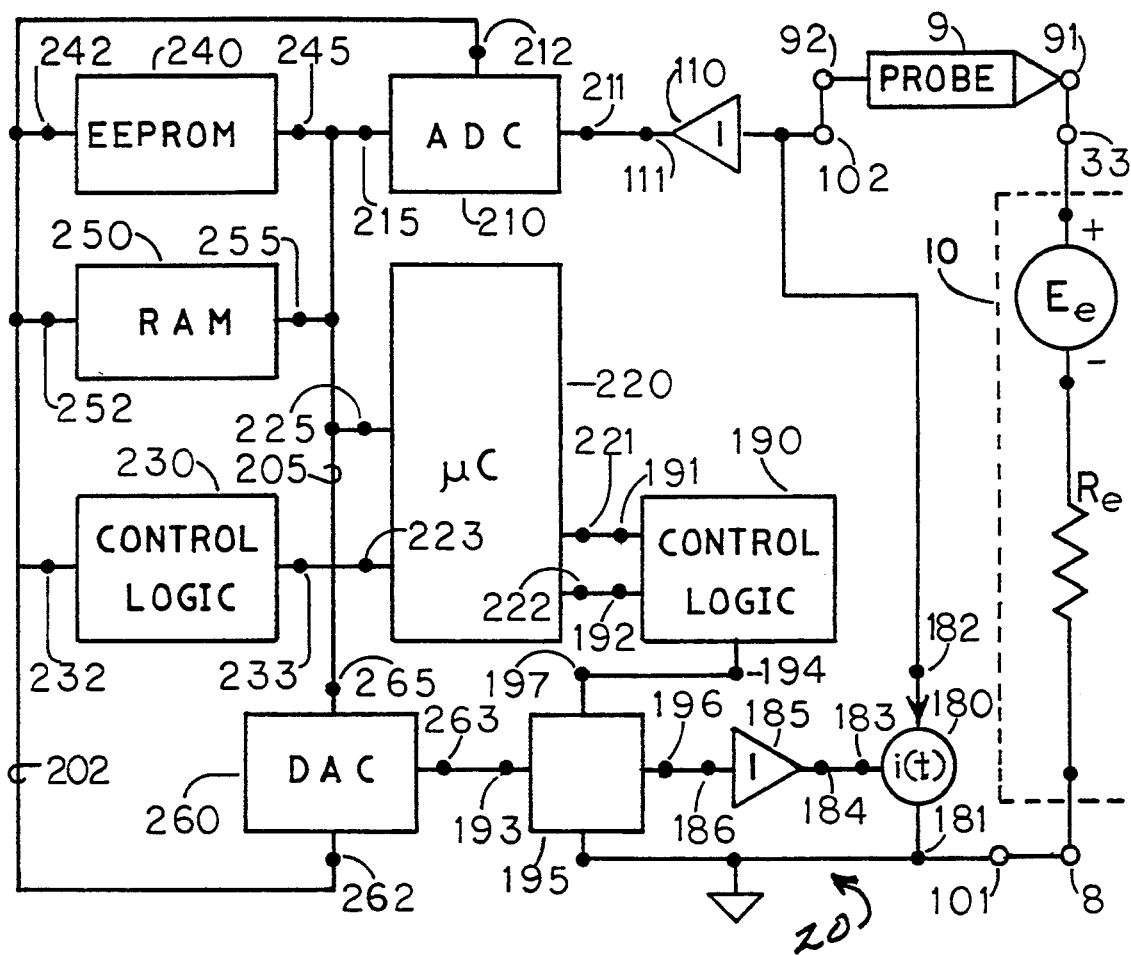
FIG. 7A shows the functional block diagram of the analyzer while the stepped current is being generated in connection with the equivalent circuit of a corrosion protected system 10 in its steady state mode and connected with the probe 9.

With reference now to FIGS. 7A and 8, the measurement of the voltage drop caused by the ground current Ig across the equivalent resistance Re will follow in detail. With reference to FIG. 7A, at the rising edge of the fourth clock pulse, the microcontroller 220 will activate the DAC 260 through the control logic 230 and the constant current generator 180 through the logic control 190 via the electronic switch 195 and unity gain amplifier 185 simultaneously. Following the activation of the DAC 260 and the current generator 180, the microcontroller 220 will inject sequentially increasing binary numbers to the input terminal 265 of the DAC 260, one at a time. After the injection of each binary number, the microcontroller 220 examines the effect on the output of the ADC 210 to check whether the voltage at the terminal 102 is zero or not. As soon as the microcontroller detects a zero voltage through its data port 225, it then will generate the fifth clock pulse while it grounds the input of the amplifier 185 through the electronic switch 195. This in return deactivates the constant current generator 180 and reduces its output current to zero while enabling the ground current Ig to take effect as transients die away.

Figure 7B:
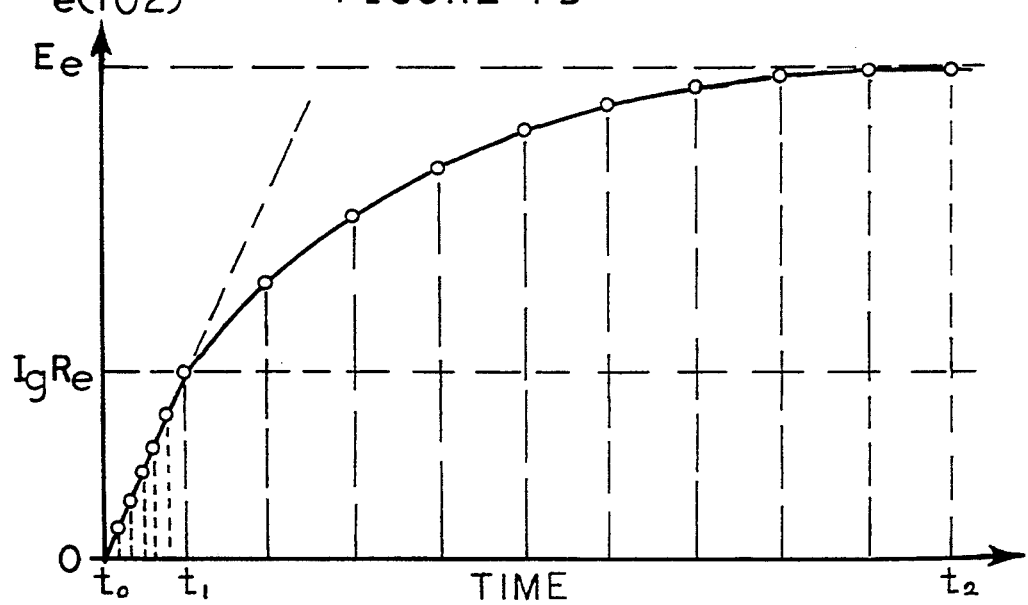
FIG. 7B shows the sampled voltage across the equivalent resistance Re as a function of time while the ground current Ig takes effect.

In reference to FIG. 7B, the voltage of the terminal 102 is digitized at the maximum rate until the inflection point is detected. The time elapsed from the rising edge of the fifth clock pulse to the time of the inflection point is detected and it becomes the timing coefficient of the depletion region capacitance Cd while the voltage corresponding to the inflection point is simply the IR Drop. As shown in FIG. 7B, the voltage rise due to the drop is linear due to the fact that the ground current Ig is constant and it charges the depletion region capacitance Cd at a constant rate. Since the hydroxyl ion concentration results from the electrolysis, it represents the charge concentration at the locale of the test point 8. Due to the lower mobility of the hydroxyl ions, the voltage at the terminal 102 will slowly and exponentially rise to its limit of Ee as a function of time.

As mentioned in the "background and summary of the invention", during the generation of the forced Off state condition around the test point 8, some of the hydroxyl ions will disappear because of recombination in the localized region. As soon as the forced Off state condition is terminated, the electrolysis controls regenerating the lost hydroxyl ions and returns the region to its balanced ionic condition. This phenomenon can be observed in measuring the equivalent resistance by sourcing a constant current pulse into the ground and by sinking a constant current pulse from the ground. That is, the sourced current pulse will generate extra hydroxyl ions, and the sunk (or reverse) current pulse removes the extra hydroxyl ions. The effect is shown in the curves in FIG. 8 as ringing in the rise and fall times.

The principle and the mode of operation of the invention have been explained and illustrated in its preferred embodiment. It must, however, be understood that the invention may be practiced otherwise than as specifically illustrated and described without departing from its spirit or scope. For example, the waveform of a constant current either being sourced or sunk may be changed in frequency or in phase during the active mode of operation, or the stepwise increasing constant current format may be substituted by a sawtooth waveform. This would not change the method of generating a forced Offstate condition or the method of measurement of the specified parameters. Furthermore, application of this invention is not restricted only to cathodic protection by electrolysis. The condition of the systems protected by the sacrificial anodes can easily be evaluated by this invention. Therefore, these changes and modifications are included within the scope and spirit of this invention, and it will be limited only by the scope of the claims appended hereto.

What is claimed is:

1. A method of measuring the cathodic activity resulting from placing a cathodic protective system on a metal structure subject to corrosion or metal loss from use in a medium having electrolytic activities sufficient to otherwise damage the structure, and the protective system includes as least one current generator connected to the metal structure and to a sacrificial metal anode exposed to the medium, said method comprising the steps of:
   (a) initimately contacting the medium with a probe having a ground connection to the metal structure at a ground point, wherein the probe contact is spaced from the ground point to define a medium dependent resistance therebetween, and the resistance of the medium is sufficient so that the current flow from at least one of the current generators flows through the medium and across the resistance thereof to enable the probe to obtain a reference voltage value:
   (b) forming a measuring current;
   (c) introducing the measuring current so that the measuring current flows through the medium between the ground point and the probe contact and further measuring the voltage induced by the measuring current at the probe;
   (d) selecting a polarity for the measuring current so that the measuring current alters the measured voltage at the probe;
   (e) changing the measuring current over a period of time, where the time period is dynamically varied, so that the probe measured voltage is altered from a reference voltage to a first voltage; and
   (f) from the first voltage, determining a characteristic of the cathodic protective system.

2. The method of claim 1 wherein the measuring current has a first polarity to obtain the first voltage, and a second polarity to obtain a second voltage, and two characteristics of the cathodic protective system are determined therefrom.

3. The method of claim 1 wherein the measuring current is fixed DC current of specific duration.

4. The method of claim 1 wherein the measuring current is varied over time wherein the time of variation is selected dynamically to optimize the accuracy and precision of the determined cathodic protection characteristic.

5. The method of claim 4 wherein the measuring current is varied to obtain a first voltage of zero.

6. The method of claim 4 wherein the measuring current is stepped over time to obtain a desired first voltage.

7. The method of claim 4 wherein the measuring current is ramped over time to obtain a desired first voltage.

8. The method of claim 1 wherein the characteristic of the cathodic protective system is measured and stored in a memory, and then a second characteristic is measured and stored.

9. The method of claim 8 wherein the stored characteristics describe the condition of the cathodic protective system.

10. The method of claim 1 wherein the characteristic of the cathodic protective system is indicative of a coating, if any, on the metal structure.

11. The method of claim 1 wherein the characteristic of the cathodic protective system is the depletion region capacitance of the metal structure.

12. The method of claim 11 wherein the first voltage value is an equivalent voltage comprising a voltage sum of the reference voltage and a polarization potential dependent upon the magnitude of the depletion region capacitance of the metal structure.

13. A method of measuring the cathodic activity resulting from placing a cathodic protective system on a metal structure subject to corrosion or metal loss from use in a medum having electrolytic activities sufficient to otherwise damage the structure, and the protective system includes at least one current generator connected to the metal structure and to a sacrifical metal anode exposed to the medium, said method comprising the steps of:
   (a) Intimately contacting the medium with a probe, wherein the probe is connected to a ground connection at a ground point on the metal structure to be protected, and wherein the probe contact is spaced sufficiently from the ground point to define a medium dependent resistance therebetween, and at least one of the current generators flows a current through the resistance to define a set of initial conditions relating to the cathodic protective system, and wherein the probe contact obtains a reference condition;
   (b) measuring the voltage polarity observed at the probe; and
   (c) forming a non-periodic current dependent on the measured polarity and directing the current through the probe and ground connections so that characteristics of the cathodic protective system are measured.

14. The method of claim 13 wherein the current has a first polarity to obtain a first voltage and a second polarity to obtain a second voltage and said voltages are measured at the probe.

15. The method of claim 13 wherein the current amplitude is selected so that specific voltages are obtained at the probe.

16. A method of measuring the cathodic activity resulting from placing a cathodic protective system on a metal structure subject to corrosion or metal loss from use in a medium having electrolytic activities sufficient to otherwise damage the structure, and the protective system includes at least one current generator connected to the metal structure and to a sacrificial metal anode exposed to the medium, said method comprising the steps of:
   (a) installing a ground connection from the metal structure at a ground point;
   (b) temporarily connecting a probe contact with the medium in the immediate vicinity of the metal structure to obtain readings thereat; and
   (c) connecting a current generator between the ground point and probe to form a non periodic current flow so that a measurement at the probe is altered from an initial condition with current from the current generator to a changed voltage as a result of current flow.

* * * * *